(12) United States Patent
Homan et al.

(10) Patent No.: US 12,251,256 B2
(45) Date of Patent: Mar. 18, 2025

(54) POSITIONING OF AN X-RAY IMAGING SYSTEM

(71) Applicant: KONINKLIJKE PHILIPS N.V., Eindhoven (NL)

(72) Inventors: Robert Johannes Frederik Homan, Batenburg (NL); Ronaldus Frederik Johannes Holthuizen, Culemborg (NL); Johan Juliana Dries, Arendonk (BE); Raoul Florent, Ville d'Avray (FR); Anindita Chatterjea, Best (NL); Edward Vuurberg, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 381 days.

(21) Appl. No.: 17/442,106

(22) PCT Filed: Mar. 26, 2020

(86) PCT No.: PCT/EP2020/058567
§ 371 (c)(1),
(2) Date: Sep. 22, 2021

(87) PCT Pub. No.: WO2020/193706
PCT Pub. Date: Oct. 1, 2020

(65) Prior Publication Data
US 2022/0160322 A1    May 26, 2022

(30) Foreign Application Priority Data
Mar. 26, 2019   (EP) .................................... 19290018

(51) Int. Cl.
*A61B 6/00*    (2024.01)
*A61B 6/46*    (2024.01)
(Continued)

(52) U.S. Cl.
CPC ............ *A61B 6/547* (2013.01); *A61B 6/4441* (2013.01); *A61B 6/469* (2013.01); *A61B 6/505* (2013.01);
(Continued)

(58) Field of Classification Search
None
See application file for complete search history.

(56) References Cited

U.S. PATENT DOCUMENTS 7,856,080 B2    12/2010    Klingenbeck-Regn
8,417,318 B2    4/2013    West
(Continued)

FOREIGN PATENT DOCUMENTS

| CN | 103976790 A | 8/2014 | |
|---|---|---|---|
| JP | H08289888 A | 11/1996 | |
| JP | 2018079304 A * | 5/2018 | ............... G06T 7/33 |

OTHER PUBLICATIONS

International Search Report and Written Opinion of PCT/EP2020/058567, dated May 6, 2020.
"Spine Navigation", Image Guided Surgery, 2017.

*Primary Examiner* — Yi-Shan Yang

(57) ABSTRACT

A device for positioning of an X-ray imaging system. The device comprises a processor configured to obtain 3D image data of a spine region of interest of a subject comprising a spine structure. The processor is further configured to select at least one vertebra of the spine structure as target vertebra; segment the target vertebra in the 3D image data including identifying at least one anatomic feature of the target vertebra; define a position of a predetermined reference line based on a spatial arrangement of the at least one anatomic feature; determine a target viewing direction of the X-ray imaging system based on the predetermined reference line; and provide the target viewing direction for the X-ray imaging system.

16 Claims, 11 Drawing Sheets

(51) Int. Cl.
  *A61B 6/50* (2024.01)
  *G06T 7/11* (2017.01)
  *G06T 7/33* (2017.01)
  *G06T 7/73* (2017.01)

(52) U.S. Cl.
  CPC .................. *G06T 7/11* (2017.01); *G06T 7/33* (2017.01); *G06T 7/73* (2017.01); *G06T 2200/04* (2013.01); *G06T 2207/10116* (2013.01); *G06T 2207/20104* (2013.01); *G06T 2207/30012* (2013.01)

(56) References Cited

U.S. PATENT DOCUMENTS

| | | |
|---|---|---|
| 2002/0061126 A1 | 5/2002 | Gerard |
| 2009/0010520 A1 | 1/2009 | Wang |
| 2012/0183122 A1 | 7/2012 | Ruijters |
| 2017/0367645 A1 | 12/2017 | Klinder |
| 2018/0028142 A1 | 2/2018 | Bhatia |
| 2018/0200002 A1 | 7/2018 | Kostrezewski |
| 2019/0290363 A1* | 9/2019 | Blau .......................... G06T 7/12 |
| 2020/0129240 A1* | 4/2020 | Singh ..................... A61B 34/10 |
| 2021/0077047 A1* | 3/2021 | Tolkowsky ............... G06T 7/33 |

* cited by examiner

POSITIONING OF AN X-RAY IMAGING SYSTEM

CROSS-REFERENCE TO PRIOR APPLICATIONS

This application is the U.S. National Phase application under 35 U.S.C. § 371 of International Application No. PCT/EP2020/058567, filed on Mar. 26, 2020, which claims the benefit of European Patent Application No. 19290081, filed on Mar. 26, 2019. These applications are hereby incorporated by reference herein.

FIELD OF THE INVENTION

The present invention relates to a device for positioning of an X-ray imaging system, to a medical imaging arrangement for spine interventions and to a method for X-ray imaging of a spine structure.

BACKGROUND OF THE INVENTION

During minimal invasive procedures, or also open procedures, X-ray imaging, e.g. fluoroscopic imaging, is used for navigation or for checks in case a navigation system is used. To be able to interpret the X-ray images, certain projections are used that may require a specific orientation of the X-ray imaging system, e.g. a C-arm device, in relation to a certain part of the anatomy of the subject. For example, during spine related interventions, a true AP (anteroposterior, i.e. from front to back of the subject) view of a vertebra may be provided; another example of a provided standard view is a true lateral view of a vertebra or a view providing a so-called Scotty dog sign of a vertebra. These viewing directions may require an exact alignment of the X-ray imaging system in relation to the subject. As an example, this may be provided by manual adjustment and may require multiple X-ray images, which adjustment adds up to the patient and operator dose, before the operator has found the right position of the C-arm. It is also cumbersome that this position can be different for each vertebra level along the spine.

SUMMARY OF THE INVENTION

There may thus be a need for an improved relative positioning of the X-ray imaging system for spine interventions.

The object of the present invention is solved by the subject-matter of the independent claims; further embodiments are incorporated in the dependent claims. It should be noted that the following described aspects of the invention apply also for the device for positioning of an X-ray imaging system, for the medical imaging arrangement for spine interventions and for the method for X-ray imaging of a spine structure.

According to the present invention, a device for positioning of an X-ray imaging system is provided. The device comprises a data storage unit, a processing unit and an output unit. The data storage unit is configured to store and provide 3D image data of a spine region of interest of a subject comprising a part of a spine structure, the spine structure comprising at least one vertebra. The processing unit is configured to select at least one vertebra of the spine structure as target vertebra. The processing unit is configured to segment at least the target vertebra in the 3D image data. The segmentation comprises identifying at least one anatomic feature of the target vertebra. The processing unit is also configured to define a position of a predetermined reference line based on a spatial arrangement of the at least one anatomic feature. The processing unit is further also configured to determine a target viewing direction of an X-ray imaging system based on the reference line. The output unit is configured to provide the target viewing direction for an X-ray imaging system.

This provides a viewing direction in which the spine structure, and in particular the selected vertebra is shown in a desired or requested way, e.g. in which minimum overlaying of the structure occurs and in which a minimum of distortion is shown. The determined target viewing direction may thus represent an optimal viewing direction. This optimal viewing direction can then be used for imaging steps. By determining an adapted optimal viewing direction, the user is supported, and the workflow is facilitated, since only a minimum input or action is required from the user. In particular, the optimal viewing direction is determined based on existing data and positioning information such that try-and-error imaging to achieve the desired X-ray view is no longer necessary. Hence, a reduction of X-ray dose to both subject and operator is achieved. The present invention thus relates to X-ray imaging and how to achieve a good positioning of the imaging system in terms of an optimal viewing direction.

According to an example, it is further provided an input unit. The input unit is configured to provide a spatial relation between the 3D image data and the X-ray imaging system. Further, the processing unit is configured to determine a spatial relation of a current viewing direction of the X-ray imaging system and the target viewing direction. The processing unit is also configured to convert the spatial relation into a movement vector. The processing unit is still further configured to control a movement of the X-ray imaging system and the subject in relation to each other according to the movement vector.

According to an example, the processing unit is configured to identify, as the at least one anatomic feature, surfaces of end plates of the at least one vertebra, and to identify a pair of pedicle portions of the at least one vertebra, and to identify a spinous process between the end plates of the at least one vertebra. The processing unit is also configured to define, as the reference line, a line running between the pedicle portions through the spinous process and also running parallel to the surfaces of the end plates.

According to the present invention, also a medical imaging arrangement for spine interventions is provided. The arrangement comprises an imaging system with an X-ray source and an X-ray detector configured to acquire X-ray images of a subject's anatomy. The arrangement also comprises a device for positioning of an X-ray imaging system according to one of the preceding examples. The X-ray source, together with the X-ray detector, and a subject are movable in relation to each other. The X-ray source, together with the X-ray detector, and the subject are movable according to a target viewing direction determined by the device for positioning of an X-ray imaging system.

According to an example, the imaging system is also configured to provide 3D data of the subject's anatomy. Further, the processing unit is configured to compute the 3D image data based on the 3D data.

According to an example, for providing the spatial relation between the 3D image data and the imaging system, at least one current 2D X-ray image is provided by the imaging system and the at least one current 2D X-ray image is registered with the 3D image data. A feature is identified in the at least one current 2D X-ray image and the feature of the at least one current 2D X-ray image is registered with a matching feature in the 3D image data. The determined target viewing direction is adapted according to the registration of the 3D image data and the at least one current 2D X-ray image. The at least one current 2D X-ray image is registered with the 3D image data on a per-vertebra basis.

According to an example, as the feature, a plurality of screws is detected. The processing unit is configured to compute a 3D reconstruction of the screws based on at least two 2D X-ray images from different directions. The processing unit is also configured to register the reconstructed screws with the 3D image data.

In an example, X-ray images, e.g. fluoroscopic images are also used to create a 3D model of the screws.

According to the present invention, also a method for X-ray imaging of a spine structure is provided. The method comprises the following steps:

a1) providing 3D image data of a spine region of interest of a subject comprising a part of a spine structure, the spine structure comprising at least one vertebra;
b) selecting at least one vertebra of the spine structure as target vertebra;
c) segmenting at least the target vertebra in the 3D image data, the segmenting comprising identifying at least one anatomic feature of the target vertebra;
d) defining a position of a predetermined reference line based on a spatial arrangement of the at least one anatomic feature; and
e1) determining a target viewing direction of an X-ray imaging system based on the reference line.

According to an example, it is further provided the following steps:

a2) providing a spatial relation between the 3D image data and the X-ray imaging system;
e2) determining a spatial relation of a current viewing direction of the X-ray imaging system and the target viewing direction and converting the spatial relation into a movement vector; and
f) moving the X-ray imaging system and the subject in relation to each other according to the movement vector.

According to an example, the segmenting in step c) comprises identifying:

c1) surfaces of end plates of the at least one vertebra; and
c2) a pair of pedicle portions of the at least one vertebra; and
c3) a spinous process between the end plates of the at least one vertebra.

The defining of the reference line in step d) comprises defining, as the reference line, a line running: between the pedicle portions, and through the spinous process, and parallel to the surfaces of the end plates.

In an example, only two of the group c1, c2) and c3) above are identified and the defining of the reference line in step d) comprises defining, as the reference line, a line fulfilling at least two of the criteria of:

running between the pedicle portions, and
running through the spinous process, and
running parallel to the surfaces of the end plates.

According to an aspect, the determination of the target viewing direction is based on anatomical landmarks defined in a segmentation step. These landmarks provide an individually determined reference line, which reference line is then taken to set the target viewing direction based on a general definition or general criteria. Hence, the adaptation of the target viewing direction, and thus the alignment to the particular subject, is provided by the segmentation plus definition of the reference line.

In an example, a medical system is provided that comprises a medical imaging system capable of making three-dimensional images of the anatomy and a potentially different medical imaging system capable of making 2D X-ray fluoro images from one or multiple directions. This imaging system is optionally tracked or integrated with a navigation system. Further, a segmentation algorithm capable of segmenting the relevant anatomical structures is provided, and a registration method that registers 2D X-ray fluoro images from one or multiple directions to the 3D anatomy on a per-vertebra basis. Still further, an algorithm to automatically apply the correct rigid registration by detecting the relevant/active vertebra is provided by using the selected procedure (step), the selected planning and/or the position of the surgical instrument, e.g. if a tracking system is used.

In another example, the system can calculate the optimal C-arm position and/or table position based on the segmentation results, the selected procedure (step), the selected planning and/or the position of the device, e.g. if a tracking system is used.

In a further example, a robotic system performs accurate surgery by applying continuously re-registration based on repeated X-ray fluoroscopy from one or multiple directions.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
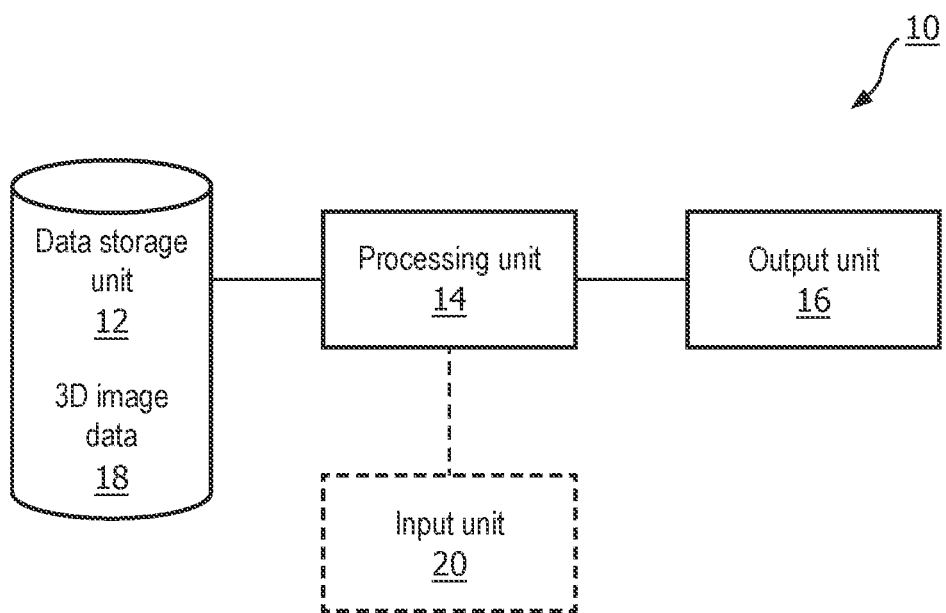
FIG. 1 schematically shows an example of a device for positioning of an X-ray imaging system.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list. FIG. 1 schematically shows an example of a device 10 for positioning of an X-ray imaging system. The device 10 comprises a data storage unit 12, a processing unit 14 and an output unit 16. The data storage unit 12 is configured to store and provide 3D image data 18 of a spine region of interest of a subject comprising a part of a spine structure, the spine structure comprising at least one vertebra. The processing unit 14 is configured to select at least one vertebra of the spine structure as target vertebra. The processing unit 14 is also configured to segment at least the target vertebra in the 3D image data. The segmentation comprises identifying at least one anatomic feature of the target vertebra. The processing unit 14 is further configured to define a position of a predetermined reference line based on a spatial arrangement of the at least one anatomic feature. The processing unit 14 is still further configured to determine a target viewing direction of an X-ray imaging system based on the reference line. The output unit 16 is configured to provide the target viewing direction for an X-ray imaging system.

In an example, the 3D image data is provided based on rotational angiography.

In an option, the 3D image data is provided as pre-operative image data.

In another option, the 3D image data is provided as intra-operative image data.

As shown with hashed lines in FIG. 1, as an option, an input unit 20 is provided. The input unit 20 is configured to provide a spatial relation between the 3D image data and the X-ray imaging system. The processing unit 14 is configured to determine a spatial relation of a current viewing direction of the X-ray imaging system and the target viewing direction. The processing unit 14 is also configured to convert the spatial relation into a movement vector. The processing unit 14 is configured to control a movement of the X-ray imaging system and the subject in relation to each other according to the movement vector.

The control of the movement of the X-ray imaging system by the processing unit is provided as an option. The control can also be provided by a separate unit or device, like an actuating unit or moving unit of the X-ray imaging system and/or an actuating unit or moving unit of a movable subject support, like a patient table.

In an example, not further shown in detail, the processing unit 14 is configured to identify, as the at least one anatomic feature, surfaces of end plates of the at least one vertebra, and to identify a pair of pedicle portions of the at least one vertebra, and to identify a spinous process between the end plates of the at least one vertebra. The processing unit 14 is also configured to define, as the reference line, a line running between the pedicle portions through the spinous process and parallel to the surfaces of the end plates.

In an example, not further shown in detail, an interface unit is provided that is configured to receive a user's input for a selection of the at least one vertebra of the spine structure as the target vertebra.

The interface unit can be provided by a keyboard, a mouse, a toggle button, a touch screen or any other suitable device.

In a further option, the selection of one or more target vertebrae is provided based on the procedure (path) planning during an intervention planning procedure using the (pre-)operative data.

In a further option, the selection of one or more target vertebrae is provided based on the current position of a device, e.g. a Jamshidi needle, probe etc., used to insert into the vertebra. The position of the device is determined using tracked devices or optical image analysis with deep learning.

In an example, not further shown in detail, the data storage unit 12 is configured to store a determined target viewing direction in relation to a subject and to use the stored determined target viewing direction for a further subject. The processing unit 14 is configured to spatially register the further subject to the X-ray system and to adapt the determined target viewing direction to a current spatial arrangement of the further subject.

Figure 2:
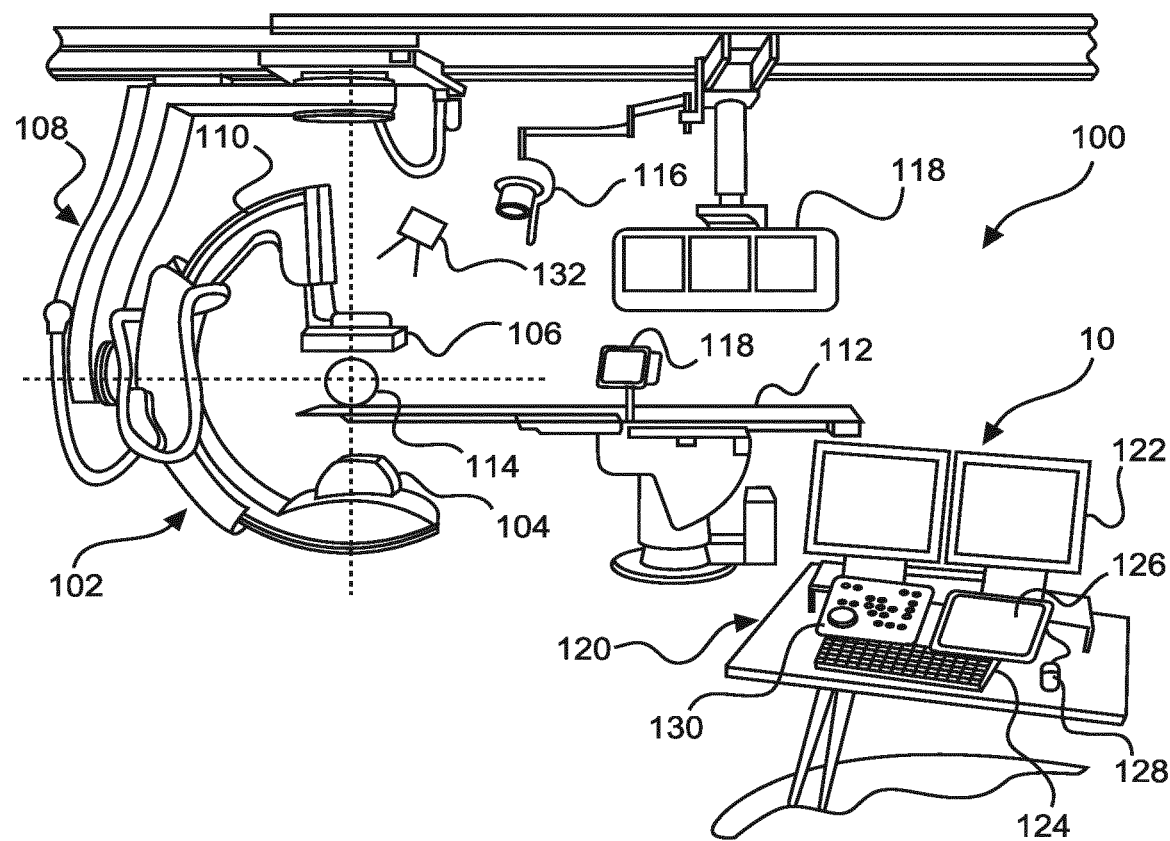
FIG. 2 shows an example of a medical imaging arrangement for spine interventions.

FIG. 2 shows a medical imaging arrangement 100 for spine interventions. The arrangement comprises an imaging system 102 with an X-ray source 104 and an X-ray detector 106 configured to acquire X-ray images of a subject's anatomy. Further, an example of the device 10 for positioning of an X-ray imaging system according to one of the preceding examples is provided. The X-ray source 104, together with the X-ray detector 106, and a subject are movable in relation to each other. The X-ray source 104, together with the X-ray detector 106, and the subject are movable according to a target viewing direction determined by the device 10 for positioning of an X-ray imaging system.

In an example, the imaging system is an X-ray imaging system.

In an example, the X-ray imaging system comprises a C-arm structure 108 with the X-ray source 102 and the X-ray detector 104 attached to opposite ends of a C-arm 110.

As a further option, a patient table 112 as a subject support is provided. An object 114 is also indicated in FIG. 2 in a simplified manner. Still further, lighting equipment 116 and additional displays 118 may be provided.

The device 10 for positioning of an X-ray imaging system is shown as a console 120 with monitors 122 and interface equipment such as keyboard 124, tablet 126, mouse 128 and other input devices like a control panel 130.

In an option, the imaging system is also configured to provide 3D data of the subject's anatomy. The processing unit 14 is configured to compute the 3D image data based on the 3D data.

In an example, the medical system is configured to automatically position the C-arm. The term "automatically" refers to a determination provided by the processing unit 14 and a steering process of the C-arm controlled by a processor to also achieve the target viewing direction. Of course, collision control equipment and other safety features may be provided. In an option, the subject support, like the patient table 112 is movable.

In an example, for performing minimal invasive spine surgery, fluoroscopic imaging is combined with 3D intra-operative imaging and navigation. The 3D intraoperative data of the spine is segmented into a model where the different parts are labeled such as each vertebra, the plates of the vertebra and the pedicles.

Due to the determined target viewing direction, provided based on the reference line, positioning the C-arm to get the required X-ray projection image is less time consuming. Since no separate X-ray image is needed for alignment of the X-ray imaging system, the patient and operator dose are reduced. The registration of the 3D image data with the patient on the one hand, and with the X-ray imaging system on the other hand, further reduces the number of X-ray projection images.

In an option, the system can store a currently used view on the segmentation and can recalculate the same view for a next subject based on the segmentation of the data of this subject. In an option, shutters are arranged to restrict the view to the segmented vertebra. In another option, the shutters are arranged to allow the view to also cover adjacent vertebrae.

In an option, the determination of the target viewing direction is provided for spinal surgery or other surgical procedures or interventional procedures in which 'standardized' projection images are used and thus pre-determined viewing directions can be defined and are provided for selection.

Provided as an option, for providing the spatial relation between the 3D image data and the imaging system, at least one current 2D X-ray image is provided by the imaging system, and the at least one current 2D X-ray image is registered with the 3D image data. A feature is identified in the at least one current 2D X-ray image and the feature of the at least one current 2D X-ray image is registered with a matching feature in the 3D image data. The determined target viewing direction is adapted according to the registration of the 3D image data and the at least one current 2D X-ray image. The at least one current 2D X-ray image is registered with the 3D image data on a per-vertebra basis.

In an example, the 3D image data is from a differing imaging system or modality. For example, the 3D image data comes from a CT scanner or an MRI scanner.

In another example, the 3D image data is from the same imaging system or modality. For example, the 3D image data comes from a C-arm X-ray imaging system also used for fluoroscopic 2D live images, that are also referred to as current images.

The registration of the at least one current 2D X-ray image with the 3D image data on a per-vertebra basis is provided as an option, e.g. to allow for bending movement of the spine.

In an example, the processing unit 14 is configured to determine positions of shutters or wedges and detector rotation based on contours of the segmented vertebra.

This results in an even further adjusted X-ray dose to the subject.

In an option, the feature is a plurality of screws. The processing unit 14 is configured to compute a 3D reconstruction of the screws based on at least two 2D X-ray images from different directions. The processing unit 14 is further configured to register the reconstructed screws with the 3D image data.

In an example, the 3D reconstruction of the screws is model-based. In addition or alternatively to screws, also other landmarks, anatomical or artificial landmarks, can be used for the registration of the 2D X-ray image with the 3D image data.

In another example, a (potentially model based) 3D reconstruction of screws is made based on fluoro shots made from two or more directions. By fusing the reconstructions of the screws onto the previously acquired image data, an extremely low-dose 3D verification scan is possible.

As an example, the previously acquired image data is based on images acquired with a flat detector C-arm volume acquisition functionality, which is integrated with the arrangement used for providing angiographic images, like a C-arm X-ray imaging system.

As an example, the previously acquired image data is based on images acquired by rotational angiography, a medical imaging technique that is based on X-ray imaging and that enables to acquire CT-like 3D volumes, e.g. during hybrid surgery or during a catheter intervention using a rigid or fixed C-arm. The C-arm rotates around the patient and acquires a series of X-ray images that are then reconstructed through software algorithms into a 3D image. This technique is also referred to as flat-panel volume CT or cone-beam CT. As an example, the previously acquired image data is based on images acquired by XperCT provided by Philips.

The fluoro registration, e.g. fluoro-XperCT registration, is used to ensure that the overlay is spatially correct in the case that the spine is deformed due to the procedure or due to the difference in the curvature of the spine with the pre-operative data.

In an option, an optical imaging system 132 is provided. The optical imaging system 132 is configured to track the subject. The processing unit 14 is configured to use a detected position of the subject for the registration steps of registering the at least one 2D X-ray image with the 3D image data. In an example, the optical imaging system comprises visible-light cameras. In another example, infrared cameras are provided.

In an example, the optical imaging system 132 is thus an optical navigation system that is used to track the position of the patient. An estimation of the position is used to initialize the registration algorithm to a) reduce the calculation time, b) prevent mis-registration to the wrong vertebral level, which can occur in particular if the field of view of the 2D or 3D information is small.

In another example, sensors of the X-ray system and the subject support, e.g. the patient table, are used to globally track the position of the patient in the X-ray images. An estimation of the position is used to initialize the registration algorithm to a) reduce the calculation time, b) prevent mis-registration to the wrong vertebral level, which can occur in particular if the field of view of the 2D or 3D information is small.

Figure 3:
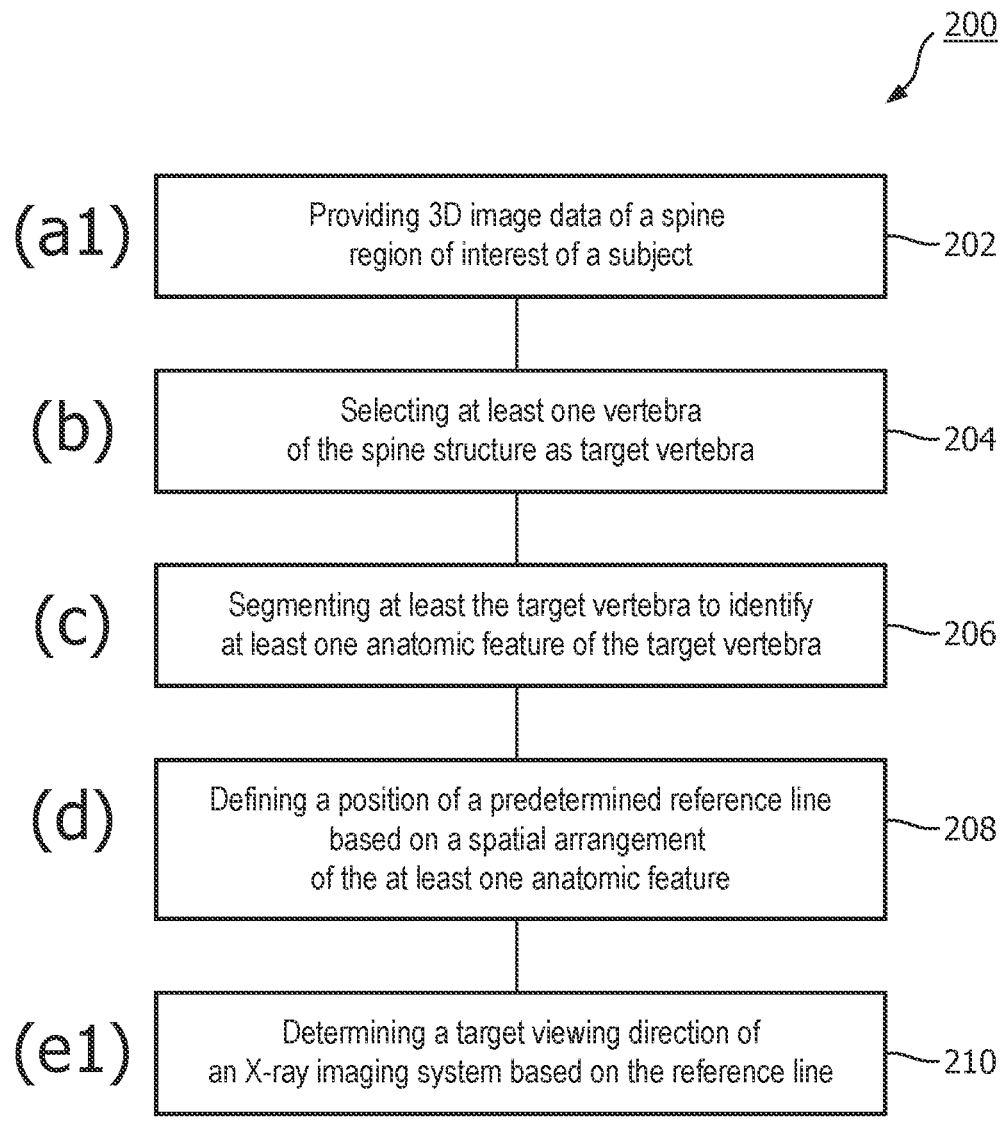
FIG. 3 shows basic steps of an example of a method for X-ray imaging of a spine structure

FIG. 3 shows basic steps of an example of a method 200 for X-ray imaging of a spine structure. The method 200 comprises the following steps:

In a first step 202, also referred to as step a1), 3D image data of a spine region of interest of a subject comprising a part of a spine structure is provided, the spine structure comprising at least one vertebra.

In a second step 204, also referred to as step b), at least one vertebra of the spine structure is selected as target vertebra.

In a third step 206, also referred to as step c), at least the target vertebra in the 3D image data is segmented. The segmenting comprises identifying at least one anatomic feature of the target vertebra.

In a fourth step 208, also referred to as step d), a position of a predetermined reference line is defined based on a spatial arrangement of the at least one anatomic feature.

In a fifth step 210, also referred to as step e1), a target viewing direction of an X-ray imaging system is determined based on the reference line.

In an option, the selecting of the at least one vertebra is provided manually.

In another option, the selecting of the at least one vertebra is provided automatically based on entered subject-related data, e.g. type and location of a planned intervention.

The target viewing direction may be defined as along the reference line.

The target viewing direction is predetermined such that an optimal view is achieved. The term "optimal" relates to a view in which the maximum amount of information is visible and in which minimum distortion or occlusion is provided. It is noted that one or several optimal viewing directions may be defined. As an example, a true AP view is provided as an optimal viewing direction. In a further example, the target viewing direction provides a true lateral view of a vertebra. In a still further example, the target viewing direction provides a view providing a so-called Scotty dog sign of a vertebra, in which the structure provides a contour that reminds of a contour of a Scotty dog.

The method thus provides a segmentation algorithm capable of segmenting the relevant anatomical structures. An algorithm is further provided that calculates the best possible C-arm position and/or subject table position based on at least one of the group of the segmentation results, the selected procedures (steps), the selected planning and the position of a device (e.g. if a tracking system is used).

The position of the predetermined reference line is spatially determined in relation to the 3D image data of the spine.

Figure 4:
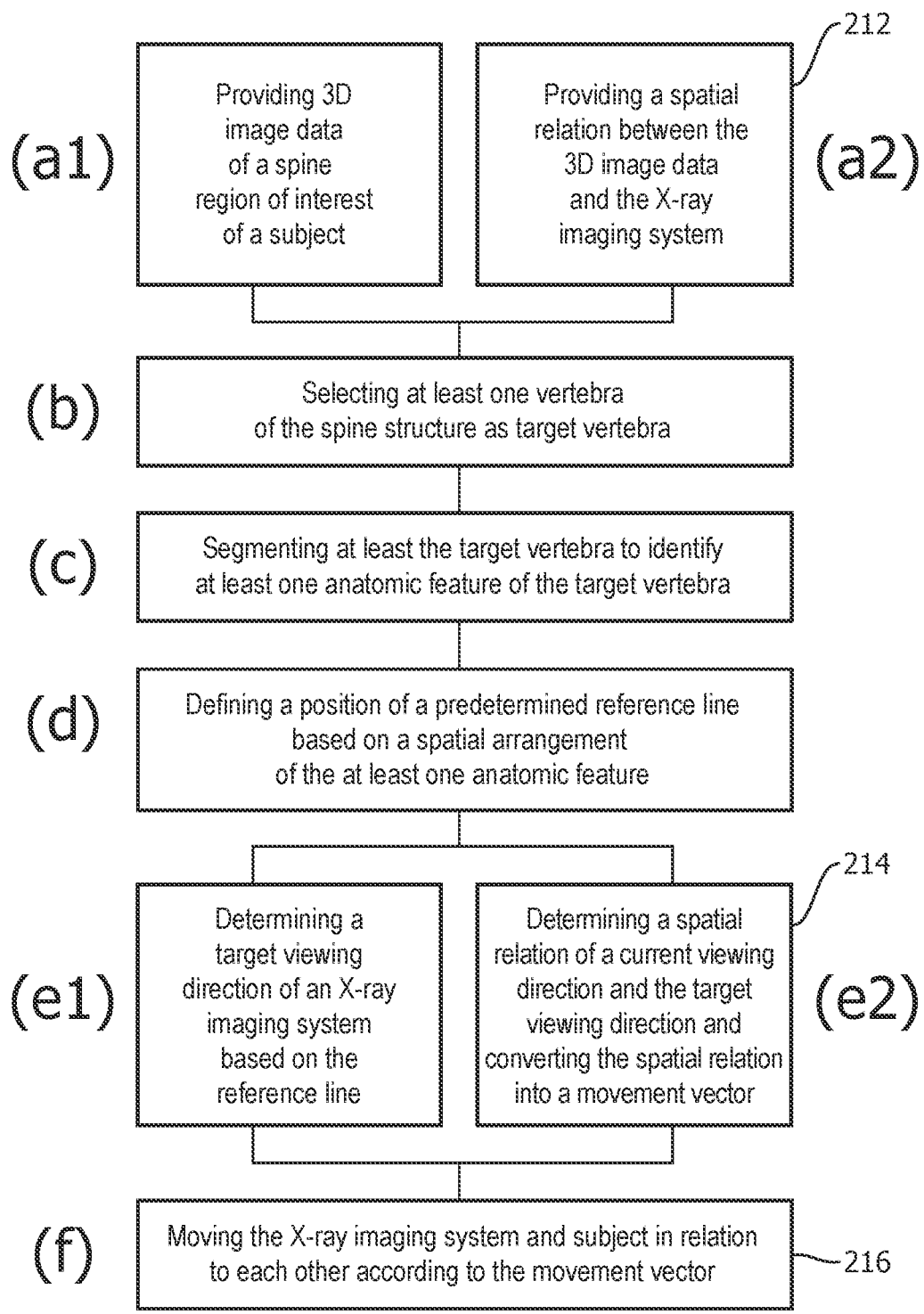
FIG. 4 shows an example of the method of FIG. 3.

FIG. 4 shows an example of the method of FIG. 3, wherein it is further provided:

In a first additional sub-step 212, also referred to as step a2), a spatial relation between the 3D image data and the X-ray imaging system is provided.

In a second additional sub-step 214, also referred to as step e2), a spatial relation of a current viewing direction of the X-ray imaging system and the target viewing direction is determining and the spatial relation is converted into a movement vector.

In an additional step 216, the X-ray imaging system and the subject are moved in relation to each other according to the movement vector.

In an option, the 3D image data is adjusted to a current position of a subject to be imaged, based on the target viewing direction.

In another option, a current position of a subject to be imaged, based on the target viewing direction, is adjusted to the 3D image data.

In a third option, a current position of a subject to be imaged, based on the target viewing direction, and the 3D image data are adjusted in relation to each other.

Figure 5:
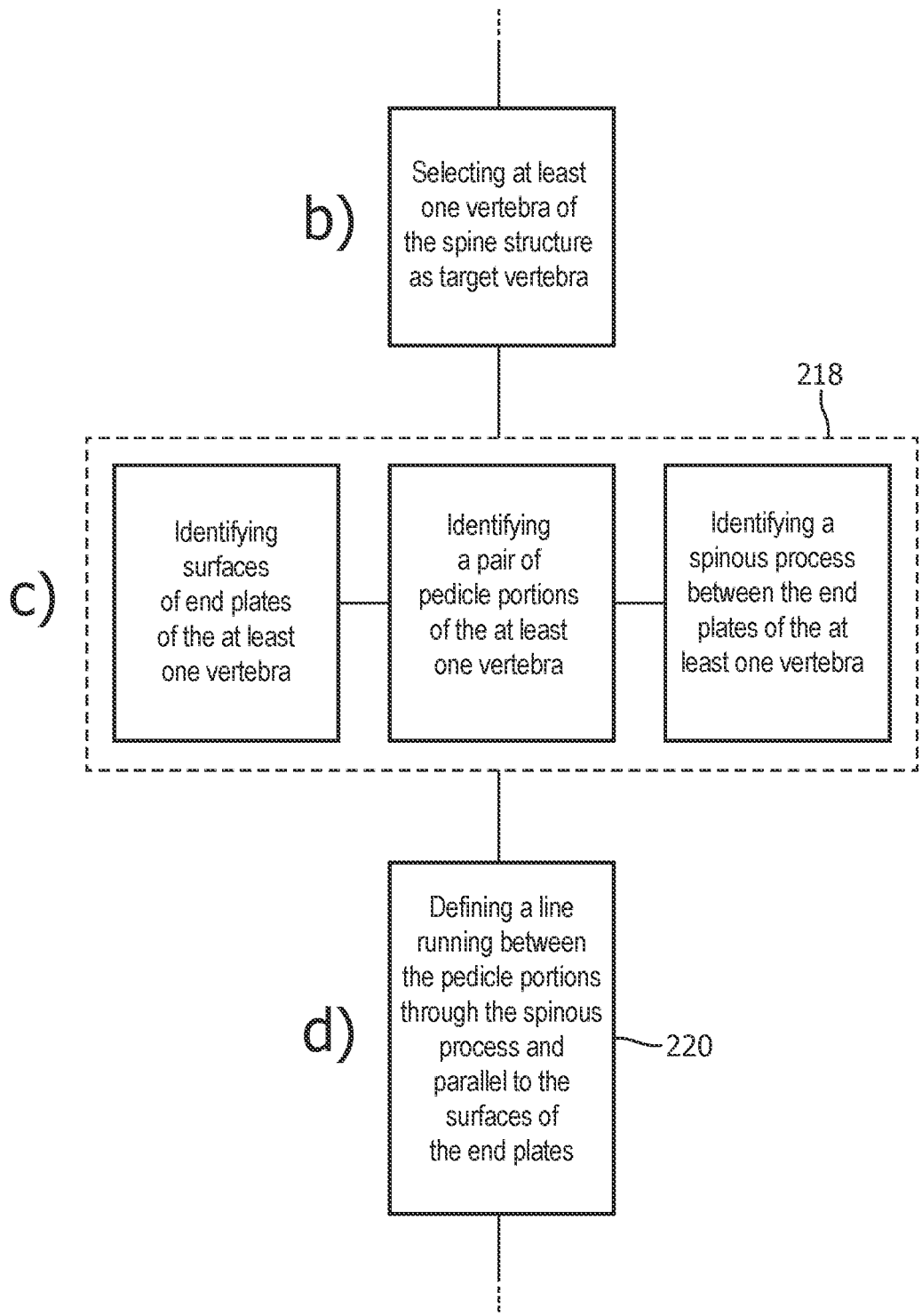
FIG. 5 shows a further example of the method of FIG. 3.

FIG. 5 shows a further example of the method of FIG. 3, wherein the segmenting in step c) comprises a step 218 of identifying:

c1) surfaces of end plates of the at least one vertebra; and
c2) a pair of pedicle portions of the at least one vertebra; and
c3) a spinous process between the end plates of the at least one vertebra.

The defining of the reference line in step d) comprises defining 220, as the reference line, a line running between the pedicle portions through the spinous process and parallel to the surfaces of the end plates.

In example, the spine comprises a plurality of vertebrae.

In an example, for a true AP view, the orientation of a C-arm is based on the normal of the end plates, both pedicles and the orientation of the spinous process.

In an example, a geometric average is calculated for the segmented features to facilitate the geometric computation of the reverence line.

In an example, step c) further comprises: determining a plane between the surfaces of the end plates, which plane runs parallel to the surfaces of the end plates, and determining a line on the plane that acts as a symmetry axis for the two pedicle portions, which line also runs though the spinous process.

In an example, the spatial relation between the 3D image data and the X-ray imaging system is provided repeatedly along the spine for at least two vertebrae.

In an example, the spatial relation is provided separately for each vertebra.

In an example, a determined target viewing direction in relation to a subject is stored and used for a further subject. The further subject is spatially registered to the X-ray system and the determined target viewing direction is adapted to the spatial arrangement of the further subject.

In an example, for a re-registration, X-ray images are acquired, and those images are also used for visual interpretation.

The target viewing direction provides an optimal view of the target vertebra.

In an example, for providing the spatial relation between the 3D image data and the X-ray imaging system, at least one current 2D X-ray image is provided by the X-ray imaging system and the at least one current 2D X-ray image is registered with the 3D image data. A feature is identified in the at least one current 2D X-ray image and the feature of the at least one current 2D X-ray image is registered with a matching feature in the 3D image data. The determined target viewing direction is adapted according to the registration of the 3D image data and the at least one current 2D X-ray image. The at least one current 2D X-ray image is registered with the 3D image data on a per-vertebra basis.

The registration on a per-vertebra basis is provided as an option.

In an example, the feature is the target vertebra.

In order to provide the spatial relation between an X-ray system that is going to be used for the imaging along the target viewing direction, the current 2D X-ray image is used. The spatial position of the X-ray system is known for that current 2D X-ray image. By registering the current 2D X-ray image with the 3D image data, the spatial link from the X-ray imaging system to the 3D space of the 3D image data is given. Thus, even when the subject moves, the registration of the current position in relation to the world of the 3D image data is given.

In an example, minimally invasive spine surgery is provided with a mobile X-ray system where pre-operative data, e.g. from CT or MRI (e.g. where a virtual CT-like dataset is calculated from the MRI images), is registered to a navigation system using one or more 2D X-ray images, such as two X-ray images. The registration process, required for surgical navigation systems, is provided by a per-vertebra registration based on the fluoroscopic images.

The registration on a per-vertebra basis is provided as an option.

In an example, an automatic and accurate per-vertebra registration of the spine anatomy is provided by using fluoro (fluoroscopic) X-ray images. This registration enables, for example, accurate surgical navigation, and also automatic positioning of mobile X-ray systems. It is also suitable for automated and accurate robotic guidance by accurate and real-time surgical navigation with constant and automatic re-registration. The correct rigid registration can be applied, e.g. automatically, by selecting the active vertebra by calculating the intersection of the planned path or tracked instrument with the spine segmentation.

The determination of the target viewing direction based on current 2D X-ray images can be applied in spinal surgery that involves 2D X-ray imaging typically combined with surgical navigation and/or robotic guidance. It is also applicable to other surgery types where the anatomy has a known spatial relationship to the spine.

In an example, the subject is tracked by an optical imaging system, and a detected position of the subject is used for the registration steps of registering the at least one 2D X-ray image with the 3D image data.

In an example, the 3D image data is provided as pre-acquisition image data or intraoperative image data.

In an example, 3D intraoperative data of the spine is provided that is segmented into a model wherein the different parts are identified, i.e. labeled, such as each vertebra, the plates of the vertebra and the pedicles.

Figure 6:
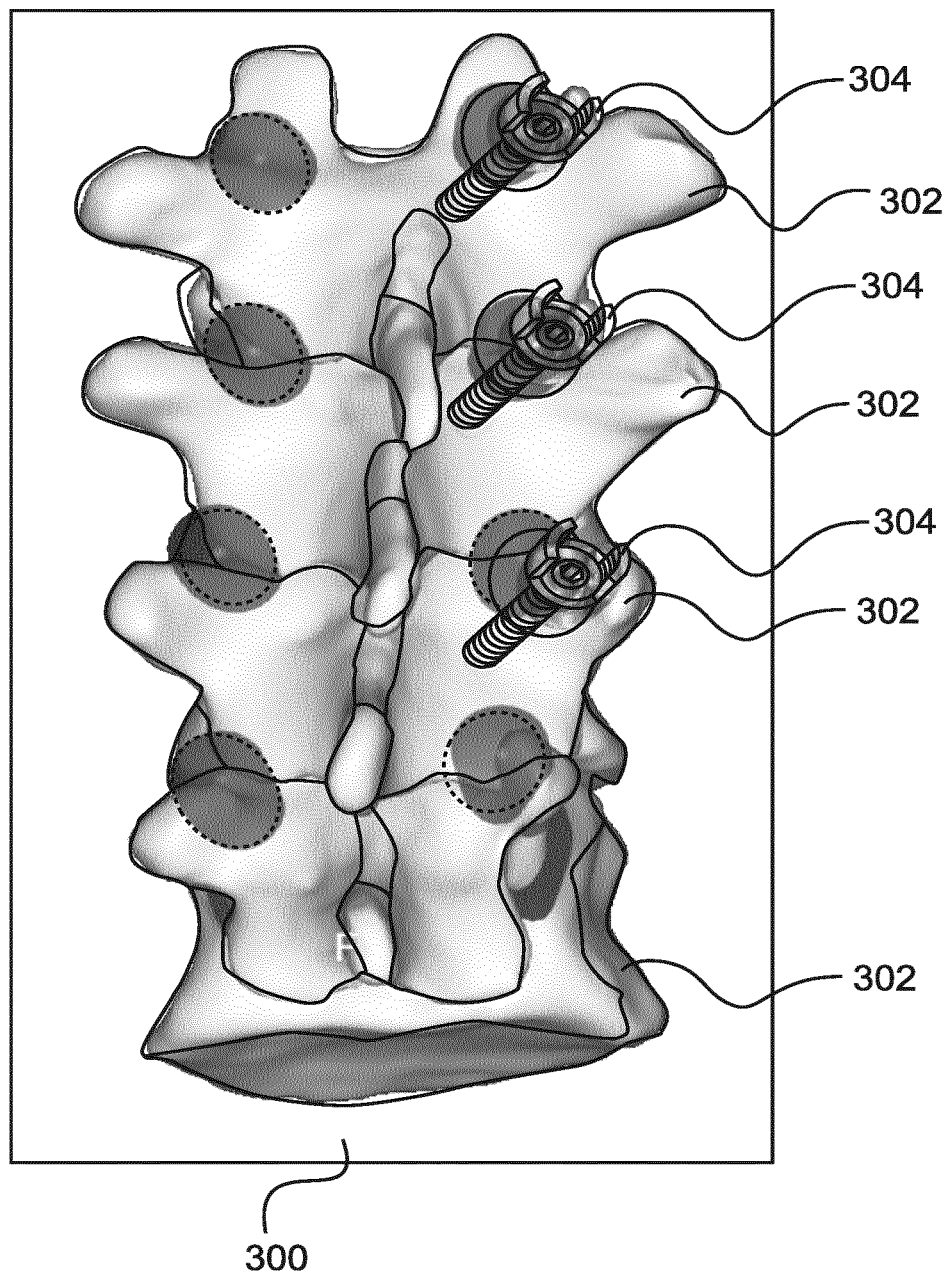
FIG. 6 shows an example of a segmented spine structure as a projection of a 3D data set.

FIG. 6 shows an example of a segmented spine structure 300 as a projection of a 3D data set. A plurality of vertebrae 302 is shown. Further, as an example, pedicle screws 304 can be seen.

Figure 7:
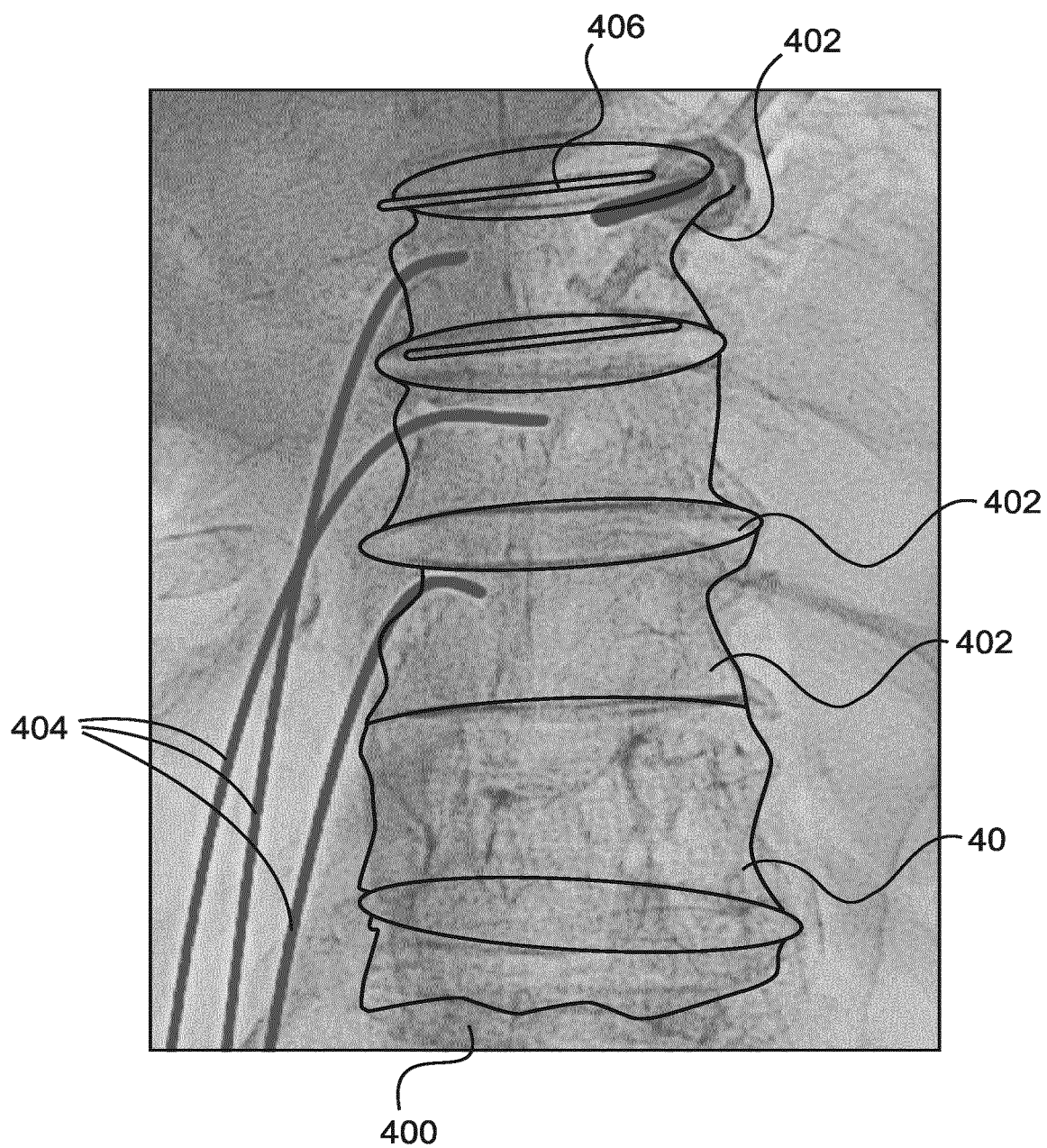
FIG. 7 shows an X-ray image with a segmented spine.

In FIG. 7, a fluoroscopic image 400 of a true AP view (anteroposterior, i.e. from front to back of the subject) is shown for a certain vertebra. In an example, the true AP view is defined as in the X-ray projection image wherein the anterior and posterior edges of vertebral end plates of a vertebra overlap in a line and the spinous process is seen between the two pedicles. The true AP view is a meaningful view for the surgeon, e.g. using the true AP view to check the position of a device, e.g. a needle or a K-wire with respect to the vertebra.

The fluoroscopic image 400 shows a plurality of vertebrae 402, and also some interventional tools 404. Two lines 406 indicate surfaces of the endplates of a selected vertebra of the plurality of vertebrae.

Figure 8:
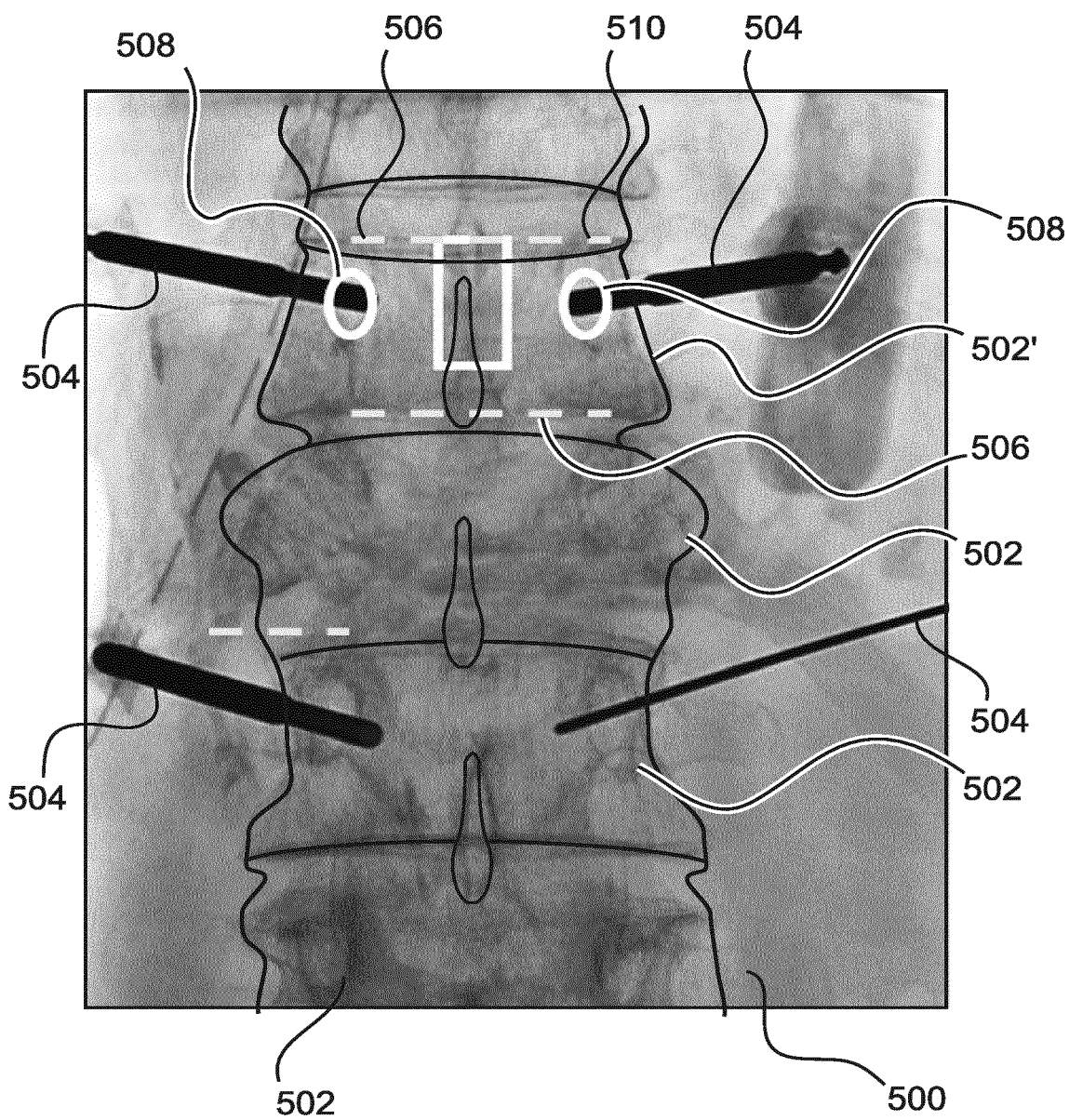
FIG. 8 shows an example of calculated orientations.

FIG. 8 shows another X-ray image 500 with a segmented spine having a plurality of vertebrae. Different interventional tools 504 are shown. In the segmented spine, a vertebra 502' is selected and the segmenting comprises identifying at least one anatomic feature of the target vertebra. As an example for the anatomic feature, two surfaces 506 of end plates of the at least one vertebra are identified. Further, a pair of pedicle portions 508 of the at least one vertebra is identified. Still further, a spinous process 510 between the end plates of the at least one vertebra is identified.

Figure 9:
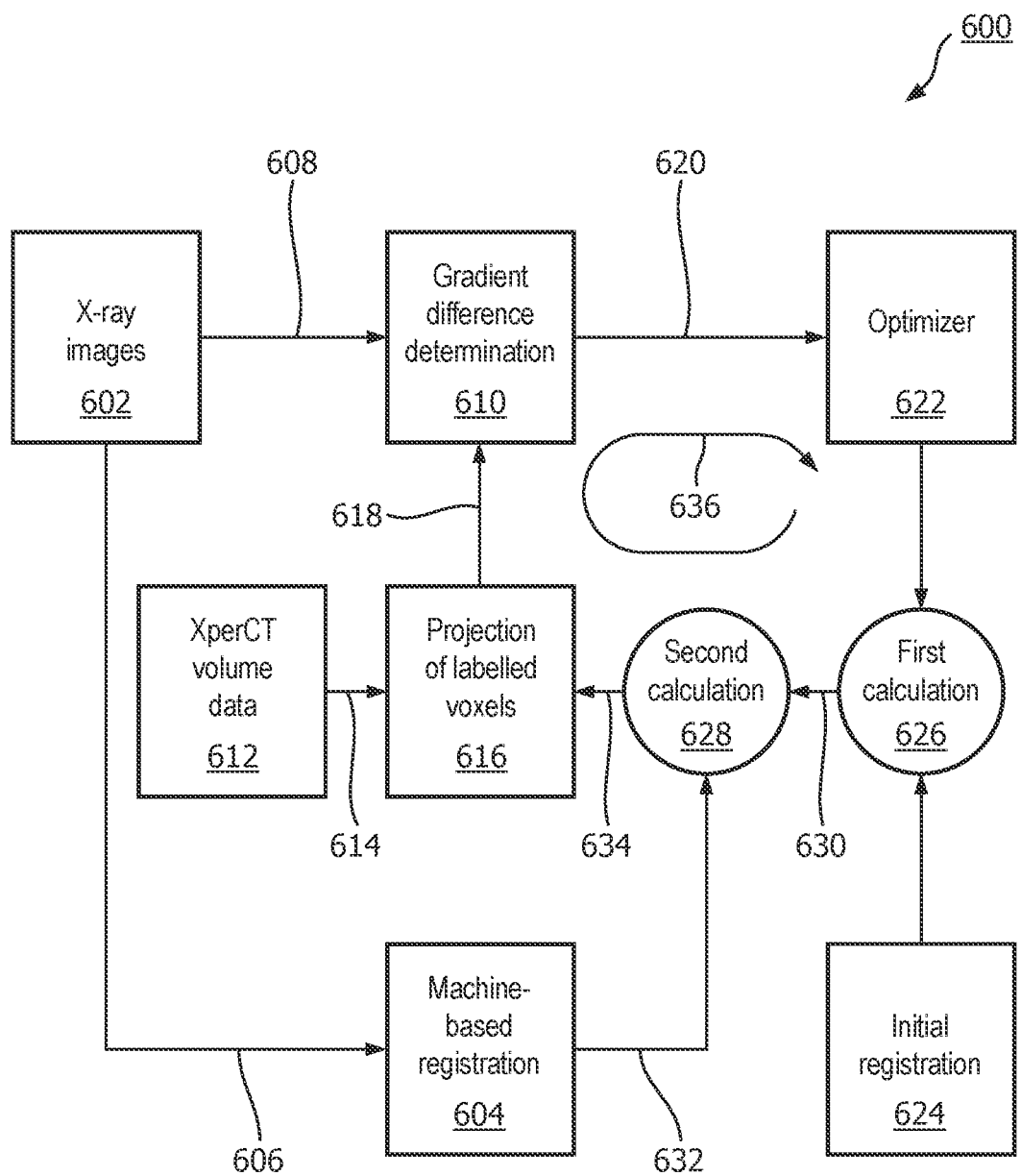
FIG. 9 shows steps of a further workflow for a 2D-3D fluoro registration algorithm.

FIG. 9 shows steps of a further workflow 600 for a 2D-3D fluoro-XperCT registration algorithm. X-ray images 602 are provided and forwarded to a machine-based registration 604. As an example, the X-ray images 602 are provided as CWIS (Collection Workflow Integration System) data 606. The X-ray images 602 are also provided, e.g. as pixels 608, to a gradient difference determination 610. Further, XperCT Volume data 612 is provided and forwarded, e.g. as voxels 614 to a projection 616 of labelled voxels, which are provided, e.g. as DRR (digitally reconstructed radiograph) pixels 618 to the gradient difference determination 610. The gradient difference determination 610 provides a result as a fitness value 620 to an optimizer 622 based on CMAES (covariance matrix adaptation evolution strategy). An initial registration 624 is provided and forwarded to a first calculation step 626 to which also the result from the optimizer 622 is provided. The result of the first calculation step 626 is provided to a second calculation step 628, e.g. as an my (matrix vision) matrix 630. The second calculation step 628 is also provided with the result of the machine-based registration 604, which may be provided as a further my (matrix vision) matrix 632. The result of the second calculation step 628 is provided to the projection 616, for example as a still further my (matrix vision) matrix 634. A circulation arrow 636 indicates that an iteration is thus provided.

In an example, these steps are used for both X-ray fluoro images and the results are combined in the optimizer 622. The voxel labelling is done on base of the spine segmentation.

In an example, the spine segmentation process is provided as a registration process that comprises a global registration step and a registration step for each "level" along the spine, i.e. each level of vertebra, to determine a deformation of the spine.

Figure 10:
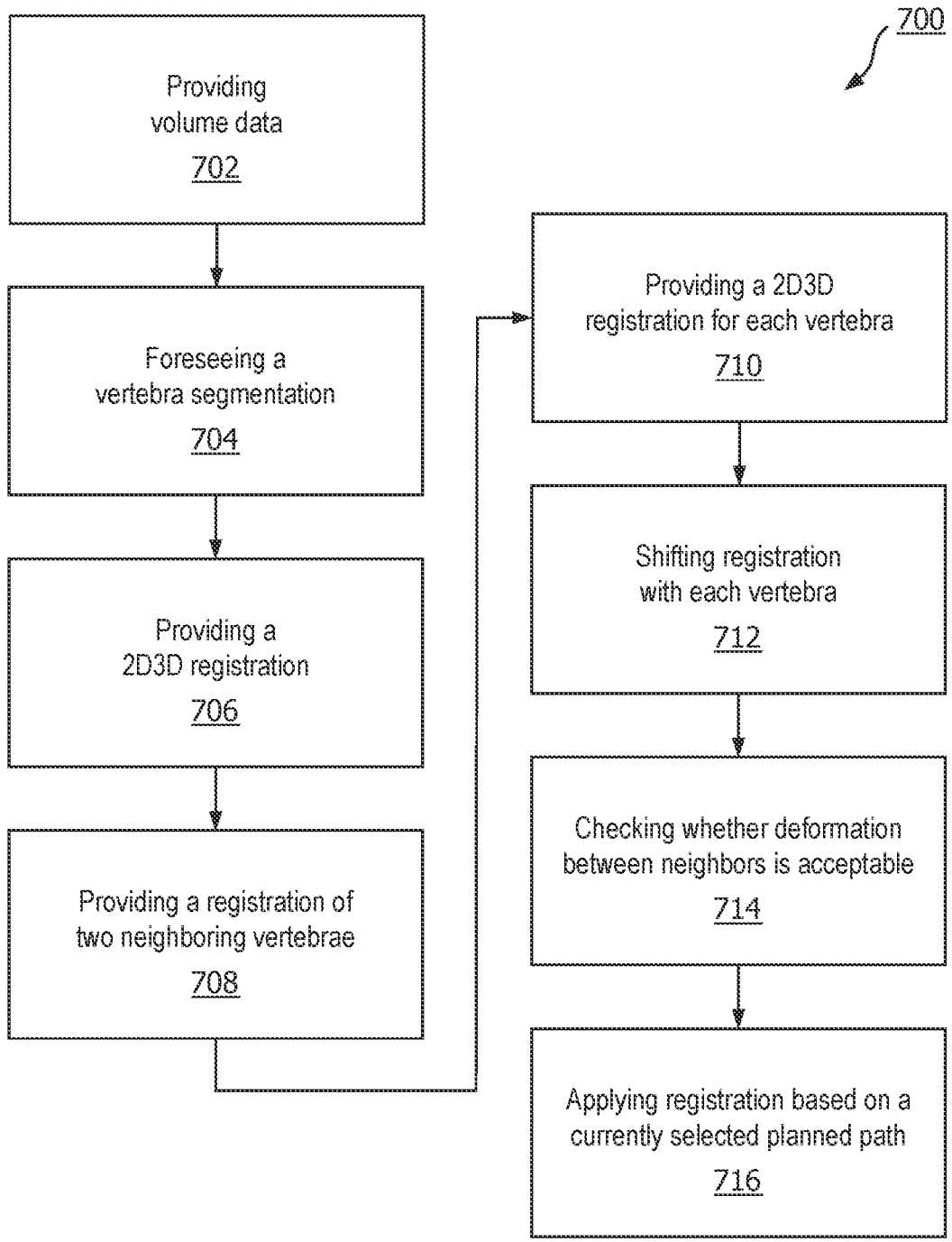
FIG. 10 shows steps of a spine segmentation process.

FIG. 10 shows a still further workflow 700 providing a spine segmentation process. For voxel labelling, in an example, the following is provided as shown. The registration process consists of several steps. As a start, volume data 702 is provided. Further, a vertebra segmentation 704 is foreseen. A 2D3D registration 706 is provided, for example with all segmented vertebrae. For example, all segmented vertebrae are registered globally. Next, a registration 708 of two neighboring vertebrae is provided, followed, as an option, by a 2D3D registration 710 for each vertebra. This is done to maximize the capture range of the algorithms. The registration with each vertebra is then shifted in a shifting step 712, which is performed to ensure that a shift of vertebrae can occur in the registration process. Each step of the registration uses the registration results of the previous step except for the registration step with one level shifted. If a registration steps fails, because not all levels give a good result, the registration step is repeated using the best registration result of all levels as starting point. After the shift, an analyzing step 714 checks whether the deformation between neighbors is acceptable. The found registrations for all vertebrae are combined. It is analyzed whether the found similarities are better as the similarities found with the shifted levels, and whether the best-found similarities are better as the worst found similarities. Following, a registration 716 is applied for the vertebra based on a currently selected planned path.

In an example, the segmentation of the vertebrae is already done for the planning work step of the surgical navigation device, so the results can be reused.

In an example, the registration step uses two automatic position control (APC) views: The 'true AP' view of the currently selected vertebra and, a rotated view to the first view (>40 degrees). For the registration itself, it is not required to use the 'true AP' view, but this view can also be used by the doctor for visual inspection. The rotated view is not completely lateral, because in most cases the table is lowered.

In an example, a user interface (UI) instructs the user to press the accept button until the C-arm stops and then acquire an X-ray image. The acquired X-ray image is shown, and the user is asked to press the accept button again until the C-arm stops and then another X-ray image is acquired. After the X-ray images are acquired, the user can start the registration.

Figure 11:
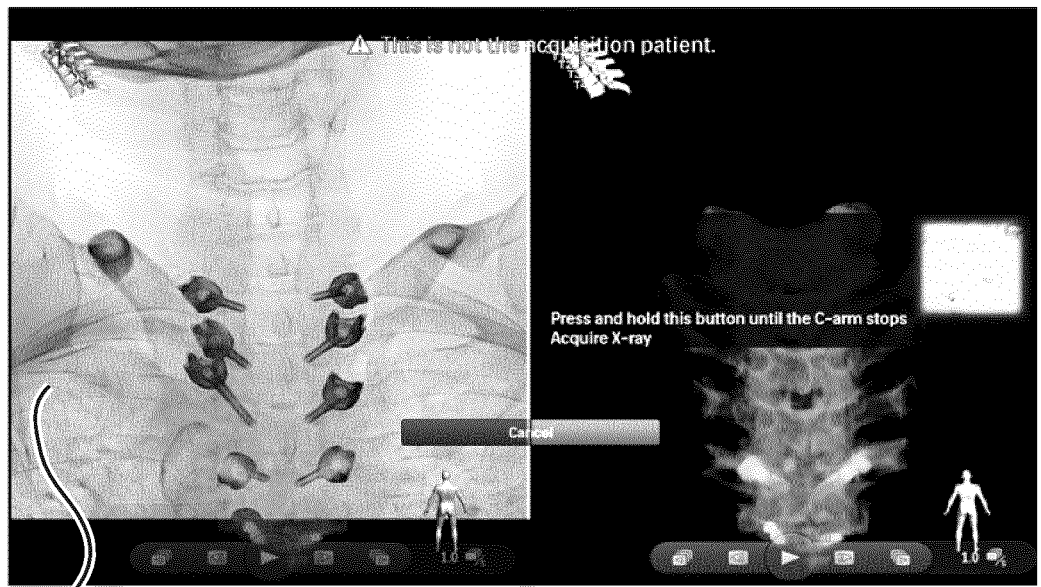
FIG. 11 schematically illustrates a screenshot for a registration user interface after acquisition of one fluoro image.

FIG. 11 schematically illustrates a screenshot 800 for a registration user interface after acquisition of one fluoro image 802.

Figure 12:
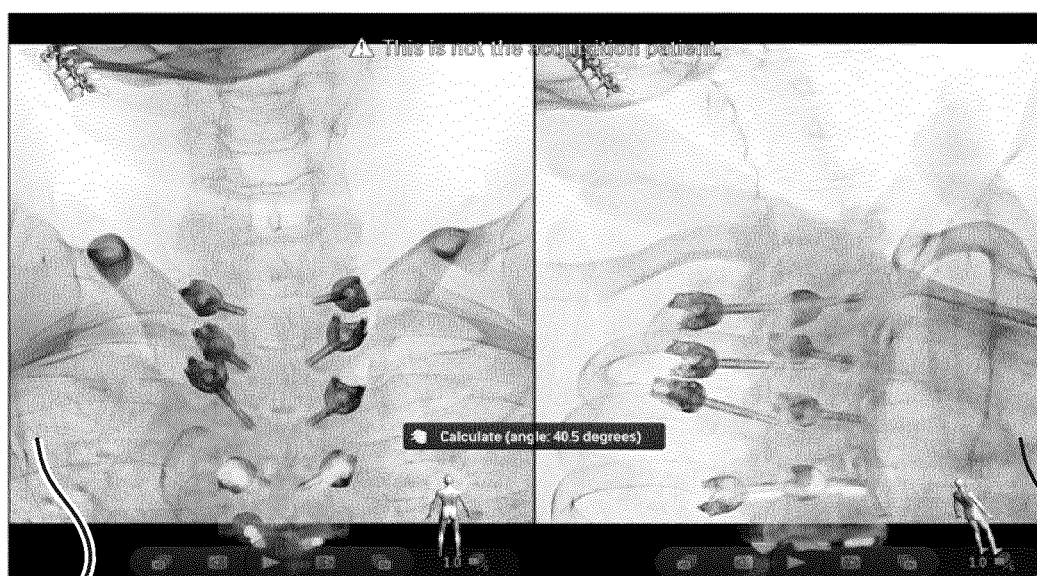
FIG. 12 schematically illustrates a screenshot after acquisition of two fluoro images.

FIG. 12 schematically illustrates a screenshot 900 for the registration user interface after acquisition of a first fluoro image 902 and a second fluoro image 904.

The found registrations are applied to the planning data and are selected based on the currently selected planned path. This means that also the APC positions are updated. In an example, it is provided that the user can visually inspect the results of the registrations. It may also be provided that a clear indication is shown to the user if the registration failed or if it is not available for the selected planned path.

The term "subject" may also be referred to as individual. The "subject" may further also be referred to as patient, although it is noted that this term does not indicate whether any illness or disease is actually present with the subject.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for positioning of an X-ray imaging system, the system comprising:
   a processor in communication with memory, the processor configured to:
     obtain three-dimensional (3D) image data of a spine region of interest of a subject comprising a spine structure;
     select at least one vertebra of the spine structure as target vertebra;
     segment the target vertebra in the 3D image data to identify at least one anatomic feature of the target vertebra, wherein the at least one anatomic feature includes end plates of the at least one vertebra;
     define a position of a predetermined reference line based on a spatial arrangement of the at least one identified anatomic feature, wherein the predetermined reference line is defined as a line running between a pair of pedicle portions of the at least one vertebra, through a spinous process between the end plates, and parallel to surfaces of the end plates;
     determine a target viewing direction of an X-ray imaging system with respect to the position of the predetermined reference line; and
     provide the target viewing direction for the X-ray imaging system; and
   the X-ray imaging system with an X-ray source and an X-ray detector, the X-ray imaging system configured to acquire X-ray images of an anatomy of the subject,
   wherein the X-ray source, together with the X-ray detector, and the subject are movable in relation to each other, and
   wherein the X-ray source, together with the X-ray detector, and the subject are movable according to the target viewing direction determined by the processor for positioning of the X-ray imaging system.

2. The system according to claim 1, wherein the processor is further configured to:
  determine a spatial relation of a current viewing direction of the X-ray imaging system and the target viewing direction;
  convert the spatial relation into a movement vector; and
  control a movement of the X-ray imaging system and the subject in relation to each other according to the movement vector.

3. The system according to claim 1, wherein the processor is further configured to receive a user's input and select the at least one vertebra of the spine structure as the target vertebra based on the user's input.

4. The system according to claim 1, wherein the processor is configured to:
  store the determined target viewing direction in relation to a subject and to use the stored determined target viewing direction for a further subject; and
  spatially register the further subject to the X-ray system and to adapt the determined target viewing direction to a current spatial arrangement of the further subject.

5. The system according to claim 1, wherein:
  the imaging system is also configured to provide 3D data of the subject's anatomy; and
  processor is configured to compute the 3D image data based on the 3D data.

6. The system according to claim 1, wherein:
  for providing a spatial relation between a current viewing direction of the X-ray imaging system and the target viewing direction, at least one current two-dimensional (2D) X-ray image is provided by the imaging system; and
  the processor is further configured to register the at least one current 2D X-ray image with the 3D image data by:
    identifying a feature in the at least one current 2D X-ray image;
    registering the feature of the at least one current 2D X-ray image with a matching feature in the 3D image data; and
    adapting the determined target viewing direction according to the registration of the 3D image data and the at least one current 2D X-ray image,
    wherein the at least one current 2D X-ray image is registered with the 3D image data on a per-vertebra basis.

7. The system according to claim 6, wherein:
  the feature is a plurality of screws; and
  the processor is configured to:
    compute a 3D reconstruction of the screws based on at least two 2D X-ray images from different directions; and
    register the 3D reconstructed screws with the 3D image data.

8. The system according to claim 1, further comprising:
  an optical imaging system configured to track a position of the subject, wherein the processor is configured to register the at least one 2D X-ray image with the 3D image data based on the tracked position of the subject.

9. A method for X-ray imaging of a spine structure, the method comprising:
  obtaining 3D image data of a spine region of interest of a subject comprising a spine structure;
  selecting at least one vertebra of the spine structure as target vertebra;
  segmenting at least the target vertebra in the 3D image data to identify at least one anatomic feature of the target vertebra, wherein the at least one anatomic feature includes end plates of the at least one vertebra;
  defining a position of a predetermined reference line based on a spatial arrangement of the identified at least one anatomic feature, wherein the predetermined reference line is defined as a line running between a pair of pedicle portions of the at least one vertebra, through a spinous process between the end plates, and parallel to surfaces of the end plates; and
  determining a target viewing direction of an X-ray imaging system with respect to the predetermined reference line,
  wherein the X-ray imaging system comprises an X-ray source and an X-ray detector, the X-ray imaging system configured to acquire X-ray images of an anatomy of the subject,
  wherein the X-ray source, together with the X-ray detector, and the subject are movable in relation to each other, and
  wherein the X-ray source, together with the X-ray detector, and the subject are movable according to the target viewing direction determined for positioning of the X-ray imaging system.

10. The method according to claim 9, further comprising:
  determining a spatial relation of a current viewing direction of the X-ray imaging system and the target viewing direction and converting the spatial relation into a movement vector; and
  moving the X-ray imaging system and the subject in relation to each other according to the movement vector.

11. The method according to claim 9, further comprising:
  obtaining a spatial relation between the 3D image data and the X-ray imaging system;
  determining a spatial relation of a current viewing direction of the X-ray imaging system and the target viewing direction;
  converting the spatial relation into a movement vector; and
  controlling a movement of the X-ray imaging system and the subject in relation to each other according to the movement vector.

12. The method according to claim 9, further comprising:
  storing a determined target viewing direction in relation to a subject and to use the stored determined target viewing direction for a further subject; and
  spatially registering the further subject to the X-ray system and to adapt the determined target viewing direction to a current spatial arrangement of the further subject.

13. A non-transitory computer-readable storage medium having stored a computer program which, when executed by a processor, causes the processor to:
  obtain 3D image data of a spine region of interest of a subject comprising a spine structure;
  select at least one vertebra of the spine structure as target vertebra;
  segment at least the target vertebra in the 3D image data to identify at least one anatomic feature of the target vertebra, wherein the at least one anatomic feature includes end plates of the at least one vertebra;
  define a position of a predetermined reference line based on a spatial arrangement of the identified at least one anatomic feature, wherein the predetermined reference line is defined as a line running between a pair of pedicle portions of the at least one vertebra, through a spinous process between the end plates, and parallel to surfaces of the end plates; and determine a target viewing direction of an X-ray imaging system with respect to the predetermined reference line, wherein the X-ray imaging system comprises an X-ray source and an X-ray detector, the X-ray imaging system configured to acquire X-ray images of an anatomy of the subject, wherein the X-ray source, together with the X-ray detector, and the subject are movable in relation to each other, and wherein the X-ray source, together with the X-ray detector, and the subject are movable according to the target viewing direction determined by the processor for positioning of the X-ray imaging system.

14. The non-transitory computer-readable storage medium according to claim 13, wherein the instructions, when executed by the processor, further cause the processor to:

provide a spatial relation between the 3D image data and the X-ray imaging system;

determine a spatial relation of a current viewing direction of the X-ray imaging system and the target viewing direction and converting the spatial relation into a movement vector; and move the X-ray imaging system and the subject in relation to each other according to the movement vector.

15. The non-transitory computer-readable storage medium according to claim 14, wherein the instructions, when executed by the processor, further cause the processor to:

obtain a spatial relation between the 3D image data and the X-ray imaging system;

determine a spatial relation of a current viewing direction of the X-ray imaging system and the target viewing direction;

convert the spatial relation into a movement vector; and control a movement of the X-ray imaging system and the subject in relation to each other according to the movement vector.

16. The non-transitory computer-readable storage medium according to claim 14, wherein the instructions, when executed by the processor, further cause the processor to:

store a determined target viewing direction in relation to a subject and to use the stored determined target viewing direction for a further subject; and spatially register the further subject to the X-ray system and to adapt the determined target viewing direction to a current spatial arrangement of the further subject.

* * * * *